US010244999B2

United States Patent
Kang et al.

(10) Patent No.: US 10,244,999 B2
(45) Date of Patent: Apr. 2, 2019

(54) THREE-DIMENSIONAL IMAGE GENERATING METHOD AND SYSTEM USING MULTI-ENERGY X-RAY IMAGE AND OPTICAL IMAGE

(71) Applicant: KOREA ELECTROTECHNOLOGY RESEARCH INSTITUTE, Changwon (KR)

(72) Inventors: Dong Goo Kang, Hwaseong (KR); Seung Oh Jin, Ansan (KR); Ki Young Shin, Seoul (KR); In Soo Kim, Seongnam (KR); Young Min Bae, Seongnam (KR); Guang Hoon Kim, Busan (KR); Bo Su Jeong, Seoul (KR)

(73) Assignee: KOREA ELECTROTECHNOLOGY RESEARCH INSTITUTE, Changwon (KR)

( * ) Notice: Subject to any disclaimer, the term of this patent is extended or adjusted under 35 U.S.C. 154(b) by 0 days.

(21) Appl. No.: 15/320,238

(22) PCT Filed: Nov. 27, 2015

(86) PCT No.: PCT/KR2015/012832
§ 371 (c)(1),
(2) Date: Dec. 19, 2016

(87) PCT Pub. No.: WO2017/082449
PCT Pub. Date: May 18, 2017

(65) Prior Publication Data
US 2018/0242939 A1    Aug. 30, 2018

(30) Foreign Application Priority Data
Nov. 13, 2015 (KR) .................. 10-2015-0159883

(51) Int. Cl.
*A61B 6/00* (2006.01)
*A61B 6/02* (2006.01)
(Continued)

(52) U.S. Cl.
CPC .............. *A61B 6/466* (2013.01); *A61B 6/025* (2013.01); *A61B 6/482* (2013.01); *A61B 6/5235* (2013.01);
(Continued)

(58) Field of Classification Search
CPC combination set(s) only.
See application file for complete search history.

(56) References Cited

U.S. PATENT DOCUMENTS 5,842,858 A * 12/1998 Truppe ................ A61B 5/06
433/69
7,292,716 B2 * 11/2007 Kim ..................... A61C 1/084
382/128
(Continued)

FOREIGN PATENT DOCUMENTS

| KR | 10-2006-0077549 A | 7/2006 |
|---|---|---|
| KR | 10-0702148 B1 | 3/2007 |

(Continued)

OTHER PUBLICATIONS

International Search Report for International Patent Application No. PCT/KR2015/012832 filed Nov. 27, 2015.

*Primary Examiner* — Tsung Yin Tsai

(57) ABSTRACT

The present invention relates to a three-dimensional surface image generating method and system using a multi-energy X-ray image and an optical image, and more particularly, to a three-dimensional surface image generating method and system using a multi-energy X-ray image and an optical image which reconstruct an X-ray tomographic image with an improved contrast of soft tissue including skin of an (Continued)

object using two or more multi-energy X-ray transmission data, calculate a three-dimensional surface model for the object, and combine optical image information including color information of the object to generate a three-dimensional surface image for the object.

20 Claims, 12 Drawing Sheets

(51) Int. Cl.
  *G06T 7/00* (2017.01)
  *A61B 6/03* (2006.01)
(52) U.S. Cl.
  CPC .......... *A61B 6/5247* (2013.01); *G06T 7/0012* (2013.01); *A61B 6/032* (2013.01); *A61B 6/4035* (2013.01); *A61B 6/481* (2013.01)

(56) References Cited

U.S. PATENT DOCUMENTS

| | | | |
|---|---|---|---|
| 7,412,024 B1 * | 8/2008 | Yun | A61B 6/484 250/367 |
| 9,025,849 B2 * | 5/2015 | Fouras | A61B 6/486 382/132 |
| 9,250,200 B1 * | 2/2016 | Grubsky | G01N 23/046 |
| 9,414,797 B2 * | 8/2016 | Flohr | A61B 6/032 |
| 2004/0247076 A1 * | 12/2004 | Navab | A61B 6/5247 378/63 |
| 2005/0135664 A1 * | 6/2005 | Kaufhold | G06T 11/006 382/131 |
| 2007/0238957 A1 * | 10/2007 | Yared | A61B 5/0059 600/407 |
| 2008/0226018 A1 | 9/2008 | Partain et al. | |
| 2010/0124367 A1 * | 5/2010 | Cizek | G06T 7/33 382/132 |
| 2011/0142316 A1 * | 6/2011 | Wang | G06T 11/006 382/131 |
| 2011/0282181 A1 * | 11/2011 | Wang | A61B 5/0095 600/407 |
| 2012/0302880 A1 * | 11/2012 | Tian | A61B 5/0035 600/427 |
| 2013/0101082 A1 | 4/2013 | Jordan et al. | |
| 2016/0100814 A1 * | 4/2016 | Schildkraut | A61B 6/032 382/131 |
| 2017/0200271 A1 * | 7/2017 | Atria | G06T 7/11 |

FOREIGN PATENT DOCUMENTS

| | | | |
|---|---|---|---|
| WO | WO 2007111669 A2 * | 10/2007 | .......... A61B 5/0059 |
| WO | WO-2007111669 A2 * | 10/2007 | .......... A61B 5/0059 |
| WO | WO 2014/150304 A1 | 9/2014 | |
| WO | WO 2015/091159 A2 | 6/2015 | |

* cited by examiner

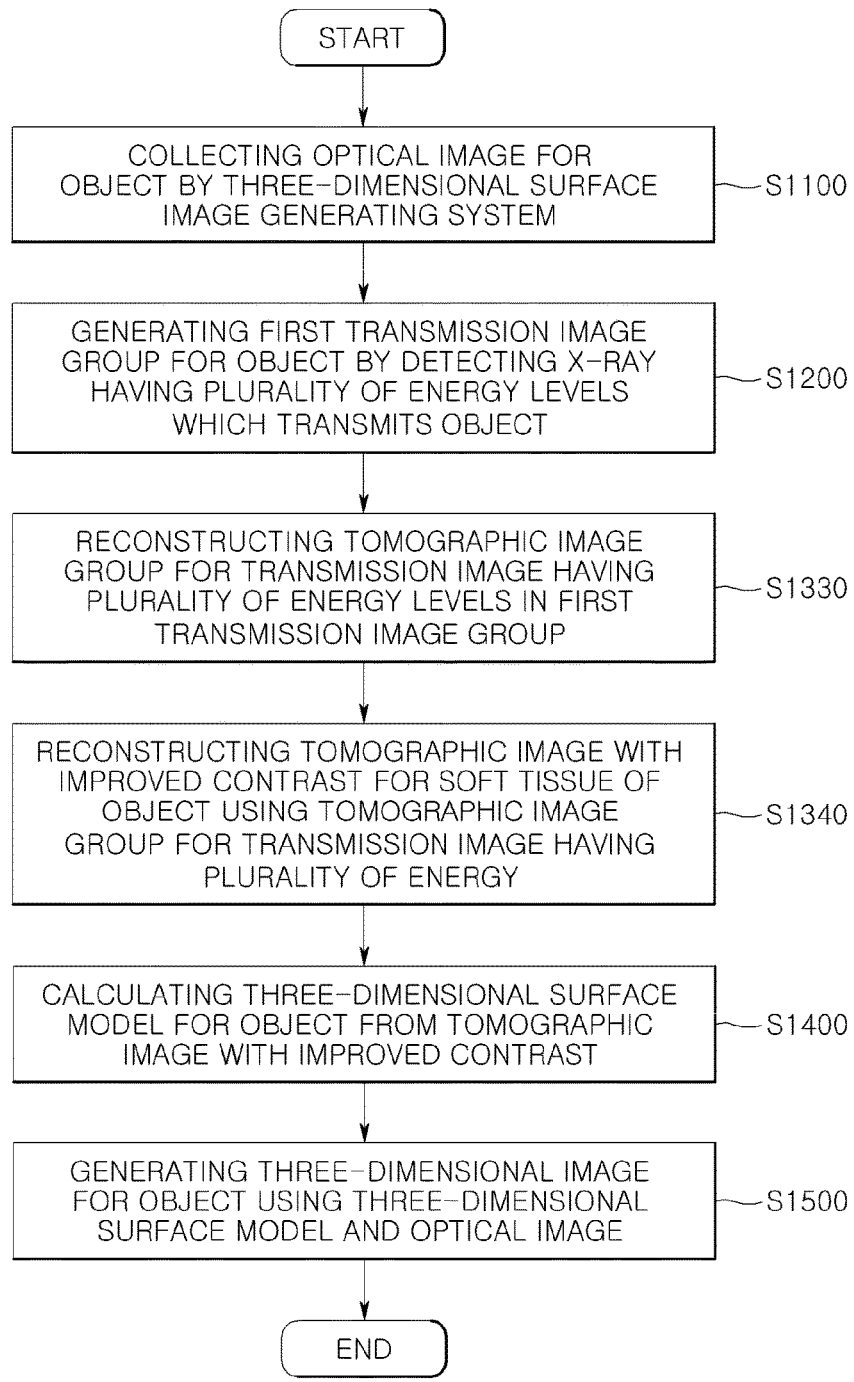

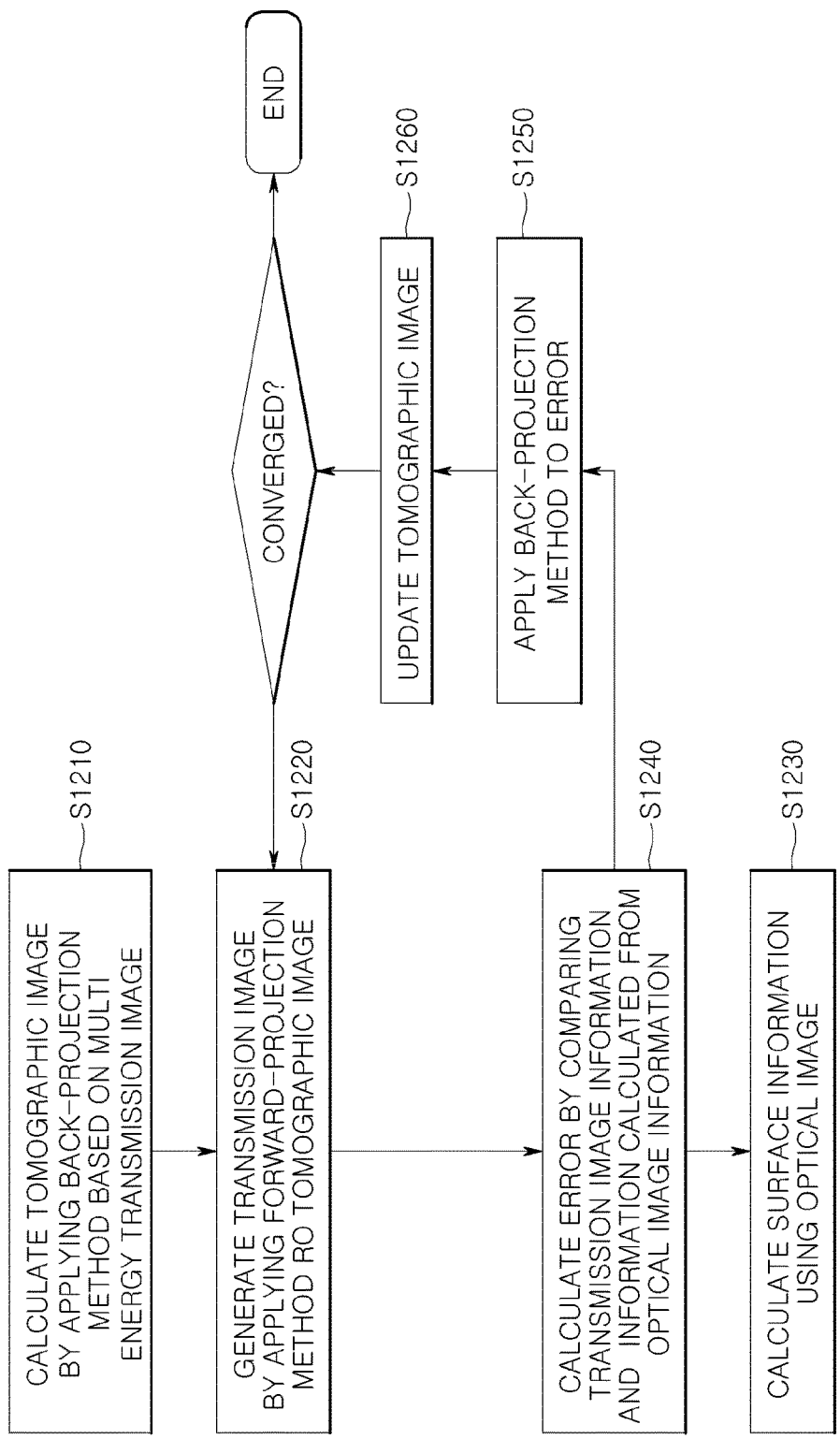

THREE-DIMENSIONAL IMAGE GENERATING METHOD AND SYSTEM USING MULTI-ENERGY X-RAY IMAGE AND OPTICAL IMAGE

CROSS REFERENCE PARAGRAPH

The present specification is a U.S. National Stage of International Patent Application No. PCT/KR2015/012832 filed Nov. 27, 2015, which claims priority to and the benefit of Korean Patent Application No. 10-2015-0159883 filed in the Korean Intellectual Property Office on Nov. 13, 2015, the entire contents of which are incorporated herein by reference.

TECHNICAL FIELD

The present invention relates to a three-dimensional image generating method and system using a multi-energy X-ray image and an optical image, and more particularly, to a three-dimensional image generating method and system using a multi-energy X-ray transmission image and an optical image which reconstruct an X-ray tomographic image with an improved contrast of soft tissue including skin of an object using two or more multi-energy X-ray transmission data, calculate a three-dimensional surface model for the object, and combine optical image information including color information of the object to generate a three-dimensional image of the object.

BACKGROUND ART

Recently, in order to make a plan for an optimal surgery method for various surgeries such as a plastic surgery, or to predict an effect of the surgery in advance, or to follow up a result of the surgery, as illustrated in FIG. 1, a device which simultaneously obtains X-ray tomographic image information of a patient and optical image information such as color image information and combines the information to be one virtual three-dimensional model to generate and provide a three-dimensional image is clinically usefully used and thus studies and commercialization of various techniques which generate and provide the three-dimensional image are being tried.

For example, Korean Patent No. 10-0702148 discloses a device which generates a three-dimensional surface image using a computed tomographic image and a camera image to simultaneously obtain a three-dimensional image and a three-dimensional surface image.

However, at an X-ray energy level (80 to 140 kVp) which is generally used during the computed tomography (CT), differently from a hard tissue such as a bone, an X-ray attenuation is significantly low in soft tissue such as skin or fat and thus a contrast of the soft tissue is significantly lowered as compared with the hard tissue. Therefore, it is difficult to detect an accurate interface of the soft tissue such as skin of an object which is required to construct a three-dimensional surface image. Further, when a three-dimensional surface model of the object is generated using camera optical images photographed at various angles, there are still technical problems in that it is difficult to obtain a highly accurate three-dimensional surface model only using an optical image processing method (for example, ambiguity of a correspondence point relationship in optical images at various angles).

As another method of the related art which generates a three-dimensional surface image, US 20120300900 A1 discloses a method of obtaining a three-dimensional surface model using a separate laser scanning device and combining the three-dimensional surface model and color information included in an optical image obtained using a camera to generate a three-dimensional surface image.

However, in this case, a separate laser scanning device which does not need to be used in an X-ray device of the related art needs to be additionally provided in order to generate a three-dimensional surface model. Further, the laser scanning device is used to irradiate various laser patterns (for example, linear patterns) onto an object, photograph the laser patterns by a camera, collect the position information of the laser patterns, and then a three-dimensional coordinate on a surface of the object is calculated using a three-dimensional geometric relationship between the laser and the camera to generate a three-dimensional surface model for the object. Therefore, manufacturing cost for configuring the above-described system is increased and an examination time for laser scanning is increased. Further, according to this method, the laser needs to be irradiated onto the object (for example, a face of a human), so that a person who gets the checkup may be uncomfortable.

DISCLOSURE

Technical Problem

The present invention has been made in an effort to provide a method which generates a three-dimensional image for an object using X-ray tomographic image information and optical image information. There are provided a three-dimensional image generating method and system using a multi-energy X-ray image and an optical image which may reduce errors incurred when a three-dimensional surface model of an object is generated using a normal computed tomographic image or a camera photographed image and thus improve accuracy for a surface of the object which is generated thereby. An object of the present invention is to provide a three-dimensional image generating method and system using a multi-energy X-ray image and an optical image which generate a three-dimensional image having a high accuracy for a surface of an object without additionally using a separate device to generate a three-dimensional surface model of the object such as a laser irradiating device.

Further, another object of the present invention is to provide a three-dimensional image generating method and system using a multi-energy X-ray image and an optical image which may generate a three-dimensional image having a high accuracy for a surface of an object while preventing discomfort of the object due to the laser irradiation.

Technical Solution

According to an aspect of the present invention, a three-dimensional image generating method includes: collecting an optical image for an object, by a three-dimensional image generating system; detecting an X-ray having a plurality of energy levels which transmits the object to generate a first transmission image group for the object; calculating a three-dimensional surface model for the object using the first transmission image group; and generating a three-dimensional image for the object using the three-dimensional surface model and the optical image.

In this case, the calculating of a three-dimensional surface model may include reconstructing a tomographic image with an improved contrast of soft tissue of the object using the first transmission image group, as compared with an example which uses a transmission image by one X-ray among X-rays having a plurality of energy levels; and calculating a three-dimensional surface model for the object from the tomographic image with an improved contrast.

Here, the reconstructing of a tomographic image with an improved contrast may include: reconstructing a tomographic image group for a transmission image of a plurality of energy levels in the first transmission image group; and reconstructing a tomographic image with an improved contrast for soft tissue of the object using a tomographic image group for a transmission image of a plurality of energy levels.

Further, the reconstructing of a tomographic image with an improved contrast may include: calculating a second transmission image with an improved contrast for a surface tissue of the object using the first transmission image group; and reconstructing a tomographic image from the second transmission image.

In this case, the plurality of energy levels may include a first energy level and a second energy level which is lower than the first energy level, and in the calculating of the second transmission image, a virtual second transmission image at a third energy level which is lower than the second energy level may be calculated.

In the calculating of the second transmission image, a first image corresponding to a photoelectric absorption basis and a second image corresponding to a Compton scattering basis may be generated, and the first image and the second image may be linearly combined to calculate a virtual second transmission image at a third energy level.

Here, the third energy level may be lower than a lowest energy level which is available in the three-dimensional image generating system.

Further, in the generating of the first transmission image group, a photon counting X-ray detector or an X-ray detector having a laminated structure which detects a plurality of energy levels may be used to simultaneously detect X-rays having a plurality of energy levels.

Further, in the generating of the first transmission image group, an X-ray may be irradiated by switching an operation mode of the X-ray source to emit the X-ray having different energy levels, switching a filter by adding a multiple filter to the X-ray source to emit the X-ray having a plurality of different energy levels, or using a plurality of X-ray sources having different energy levels.

Further, in the calculating of a three-dimensional surface model, a surface detecting algorithm may be applied to the tomographic image to calculate the three-dimensional surface model.

In this case, one point or a partial region of an empty space (air) obtained by excluding a region of the object from the tomographic image may be considered as a seed and a surface of the soft tissue may be set as a limit of the region to perform a 3D region growing method and detect an interface between the empty space and the soft tissue, thereby calculating the three-dimensional surface model.

Further, in the calculating of a three-dimensional surface model, a three-dimensional surface model for the object may be corrected based on surface interface information by the first transmission image and surface contour information calculated from the optical image.

Here, the calculating of a three-dimensional surface model may include a first step of calculating an error of the surface interface information by the tomographic image and the surface contour information calculated from the optical image; a second step of updating the tomographic image by reflecting the error; and a step of repeating the first step and the second step until the updated tomographic image satisfies a predetermined convergence condition.

Further, in the generating of the first transmission image, the surface contour information of the object calculated from the optical image and preshot X-ray image information for the object may be compared to adjust X-ray exposure so that the X-ray detector operates on the surface of the object in a dynamic range where the soft tissue information is included in the first transmission image group as much as possible.

Further, an X-ray exposure setting value required to calculate the three-dimensional surface model for the object in accordance with a characteristic of the object may be stored in advance, and the X-ray exposure setting value may be applied in consideration of the characteristic of the object figured out using the optical image on the object.

The optical image may include information on a structure of a surface lower part of the object using infrared ray.

Further, the optical image may include one or more of images using visible ray or infrared ray and a spectroscopic image.

The three-dimensional image may include anatomical information or lesion information on a nerve, a blood vessel, or a specific soft tissue or contrast enhanced lesion information.

According to another aspect of the present invention, a three-dimensional image generating system, which generates a three-dimensional image for an object, includes: an optical image collecting unit which collects an optical image for an object; a first transmission image generating unit which detects an X-ray having a plurality of energy levels which transmits the object to generate a first transmission image group for the object; a three-dimensional surface model calculating unit which calculates a three-dimensional surface model for the object using the first transmission image group; and a three-dimensional image generating unit which generates a three-dimensional image for the object using the three-dimensional surface model and the optical image.

In this case, the three-dimensional surface model calculating unit may include: a tomographic image reconstructing unit which reconstructs a tomographic image with an improved contrast of the soft tissue of the object using the first transmission image group, as compared with an example which uses a transmission image by one X-ray among X-rays having a plurality of energy levels; and a three-dimensional surface model generating unit which generates a three-dimensional surface model for the object from the tomographic image with an improved contrast.

Here, the tomographic image reconstructing unit may include: a second transmission image calculating unit which calculates a second transmission image with an improved contrast for soft tissue of the object using the first transmission image group; and a tomographic image calculating unit which reconstructs and calculates a tomographic image for the object from the second transmission image.

Further, the tomographic image reconstructing unit may include: a tomographic image group reconstructing unit which reconstructs a tomographic image group for a transmission image of a plurality of energy levels in the first transmission image group; and a tomographic image generating unit which generates a tomographic image with an improved contrast for soft tissue of the object using a tomographic image group for a transmission image of a plurality of energy levels.

Advantageous Effects

According to the present invention, it is possible to reconstruct an X-ray tomographic image with an improved contrast of the soft tissue including skin of an object using two or more multi-energy X-ray transmission data, calculate a three-dimensional surface model of the object, and combine optical image information, such as color information, on the object to generate a three-dimensional image for the object, thereby reducing an error incurred when a three-dimensional surface model of the object is generated using a general computed tomographic image or camera photographed image and generating a three-dimensional image with improved accuracy on the surface of the object generated thereby.

Further, according to the present invention, the three-dimensional surface model for the object is generated using a multi-energy X-ray transmission image and an optical image without using a separate laser irradiating device so that a three-dimensional image having a high accuracy for a surface of an object may be generated without additionally using a separate device to generate a three-dimensional surface model and further discomfort of the subject due to the laser irradiation can be prevented.

DESCRIPTION OF DRAWINGS

Accompanying drawings which are included as a part of the detailed description for understanding of the present invention provide an exemplary embodiment of the present invention and describe a technical spirit of the present invention in conjunction with the detailed description.

FIG. 7 is a flowchart of a method of correcting a three-dimensional surface model for an object using an optical image according to an exemplary embodiment of the present invention.

FIG. 8 is a flowchart of a detailed three-dimensional image generating method according to another exemplary embodiment of the present invention.

BEST MODE

Figure 1:
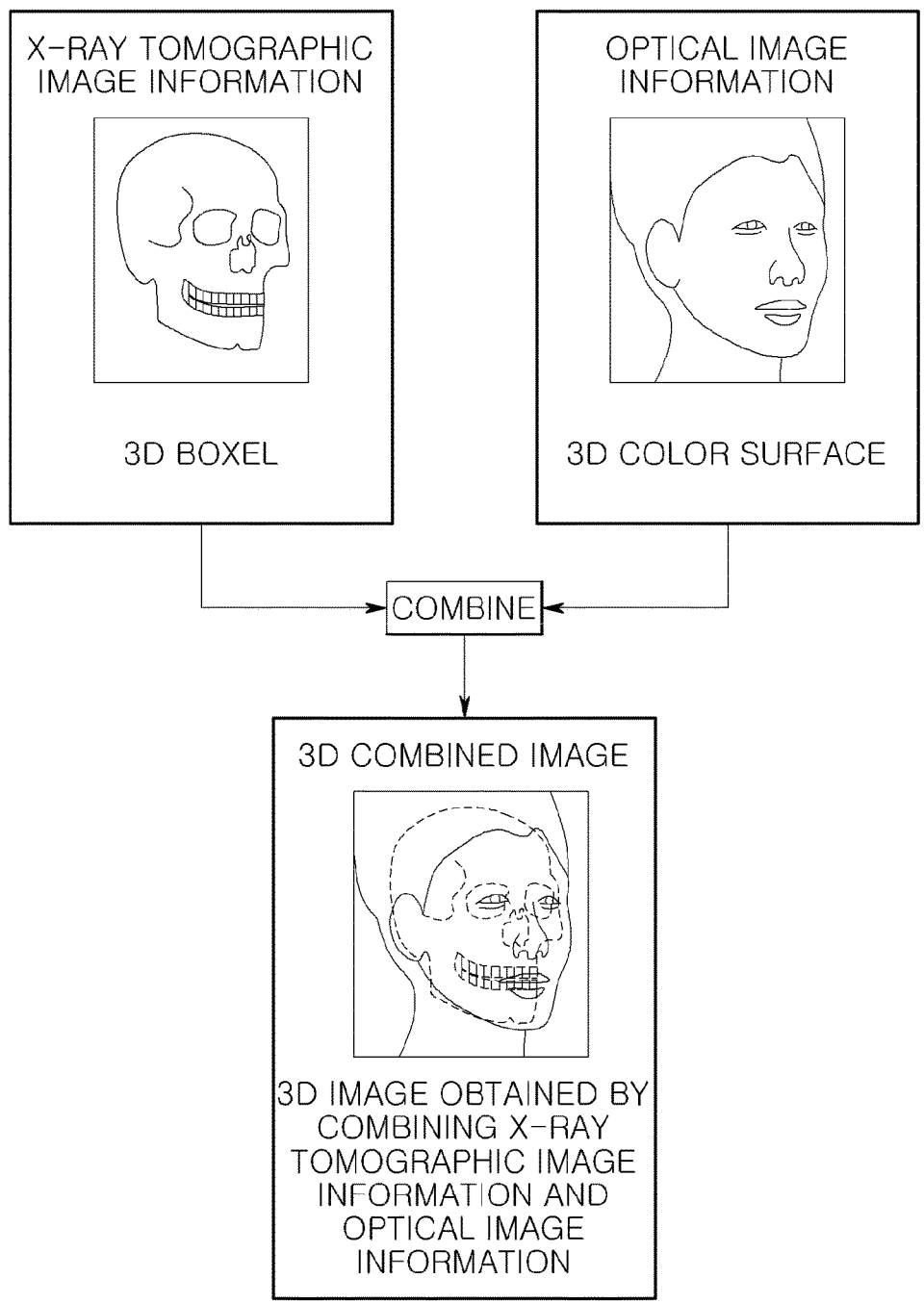
FIG. 1 is a view provided to explain a three-dimensional image in which an X-ray tomographic image and an optical image are combined according to the related art.

Those skilled in the art may make various modifications to the present invention and the present invention may have various embodiments thereof, and thus specific embodiments will be described in detail with reference to the accompanying drawings.

The following exemplary embodiments are provided for full understandings for a method, a device and/or a system described in the specification. However, the exemplary embodiments are illustrative and the present invention is not limited thereto.

In the following description of exemplary embodiments of the present invention, a detailed explanation of known related functions and constitutions may be omitted so as to avoid unnecessarily obscuring the subject matter of the present invention. Further, the terms used in the description are defined considering the functions of the present invention and may vary depending on the intention or usual practice of a user or operator. Accordingly, the terms need to be defined based on details throughout this specification. The terms used in the detailed description are used to describe the exemplary embodiments of the present invention, but are not restrictively used. Singular expressions used in the present invention include plurals expressions unless they have definitely opposite meanings. In the present invention, a term such as "comprising" or "including" particularly includes some features, numbers, steps, operations, elements, some or combination thereof and it should not be analyzed that presence or a possibility of one or more features, numbers, steps, operations, elements, some or combination thereof other than those disclosed in the specification are excluded.

In addition, terms, such as 'first' and 'second' can be used to describe various components, but the components should not be limited by the terms. The above terms are used only to discriminate one component from the other components.

In consideration of problems of the related art in that when the three-dimensional surface model is generated using a computer tomographic image or a camera image according to the related art, an error may be significant and when the laser irradiation is used, a manufacturing cost may be increased due to the increased complexity of the system and discomfort of a user may be caused, the present invention provides a three-dimensional image generating method and system using a multi-energy X-ray image and an optical image which reconstruct an X-ray tomographic image with an improved contrast of the soft tissue including the skin of an object using two or more multi-energy X-ray transmission data, calculate a three-dimensional surface model for the object, and combine optical image information including color information of the object to generate a three-dimensional image of the object, thereby generating a three-dimensional image with improved accuracy on the surface of the object and preventing discomfort of the object due to the laser irradiation without additionally using a separate device.

Hereinafter, exemplary embodiments of a three-dimensional image generating method and system using a multi-energy X-ray image and an optical image according to the present invention will be described in detail with reference to the accompanying drawings.

Figure 2:
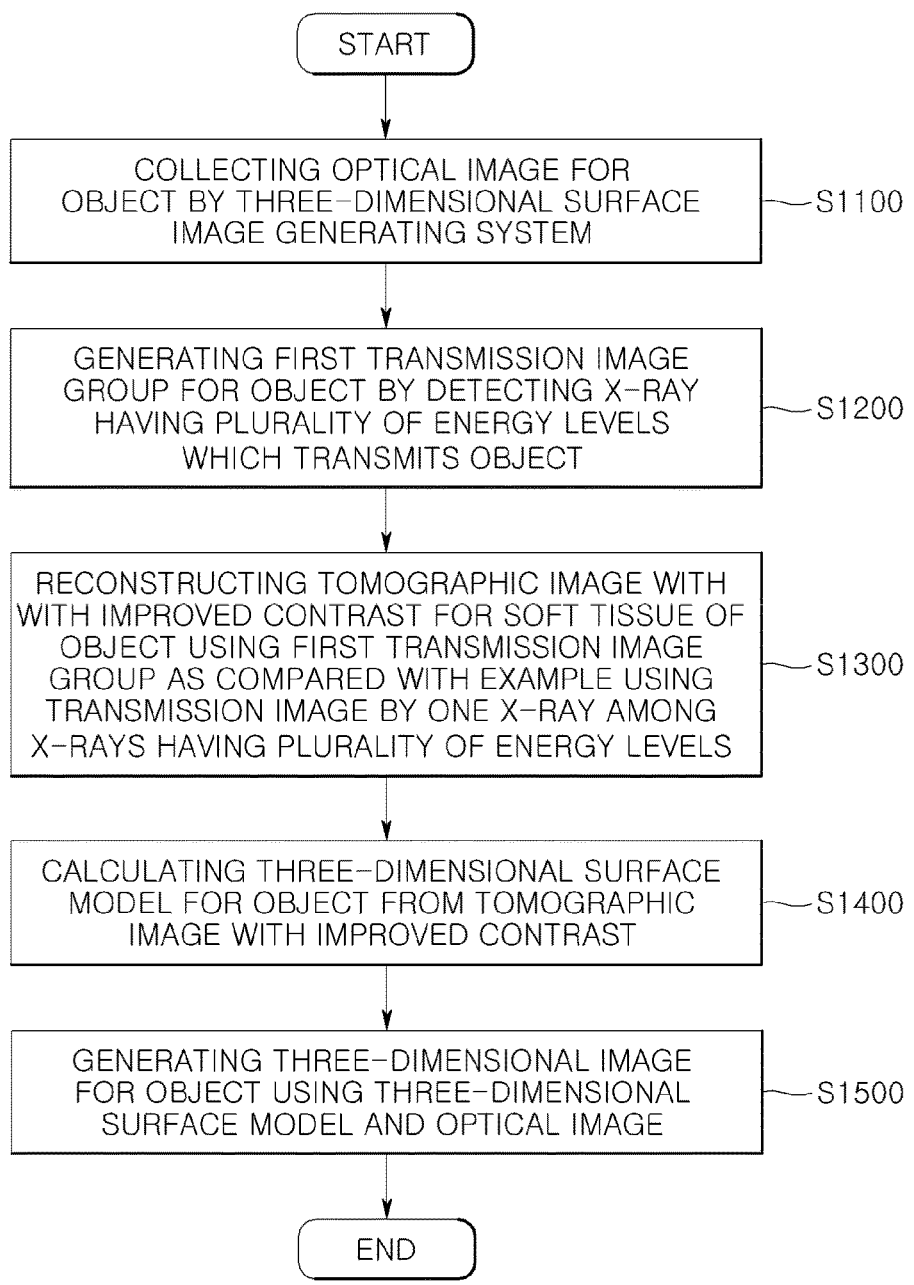
FIG. 2 is a flowchart of a three-dimensional image generating method according to an exemplary embodiment of the present invention.

First, FIG. 2 illustrates a flowchart of a three-dimensional image generating method according to an exemplary embodiment of the present invention. As illustrated in FIG. 2, the three-dimensional image generating method according to an exemplary embodiment of the present invention includes a step S1100 of collecting an optical image for an object by a three-dimensional image generating system, a step S1200 of generating a first transmission image group for the object by collecting an X-ray having a plurality of energy levels which transmits the object, a step S1300 of reconstructing a tomographic image in which a contrast of the soft tissue of the object is improved as compared with an example in which a transmission image by an X-ray among X-rays having the plurality of energy levels using the first transmission image group, a step S1400 of calculating a three-dimensional surface model for the object from the tomographic image with the improved contrast, and a step S1500 of generating a three-dimensional image for the object using the three-dimensional surface model and the optical image.

Individual steps of the three-dimensional surface image generating method according to an exemplary embodiment of the present invention will be described in more detail.

First, in step S1100, an optical image including surface color information for an object is collected. For example, an image information obtaining device such as a camera is mounted on rotator or a gantry of a computer tomography device to obtain optical image information including surface color information for the object in various directions while rotating around the object. However, it is not necessary to continuously collect the optical image in various directions of the object in step S1100 and if necessary, only a small number of optical images with respect to some directions having high importance may be collected.

The optical image collected in step S1100 is combined with a three-dimensional surface model for an object calculated from a multi-energy X-ray image to generate a three-dimensional image including surface color information. Further, the optical image collected in step S1100 may be used to correct an error of the three-dimensional surface model for the object calculated from the multi-energy X-ray image, which will be described in detail below.

Next, in step S1200, X-rays having a plurality of energy levels which transmit the object are detected to generate a first transmission image group for the object. In this case, the X-rays having a plurality of energy levels may be detected in this step using various configurations. For example, an X-ray detector which configures a photon counting X-ray detector which discerns and measures an energy level for an incident photon or an X-ray detector in which detectors which detect a plurality of energy levels form a laminated structure is used to simultaneously detect X-rays having a plurality of energy levels. Further, an operation mode of an X-ray source is switched to emit X-rays having different energy levels (for example, 80 kVp and 120 kVp) or multiple filters are added to the X-ray source to switch the filters to emit X-rays having different energy levels. Furthermore, a system including the plurality of X-ray sources having different energy levels may be configured.

In addition to the above-described configuration, a configuration which detects an X-ray having a plurality of energy levels which transmits the object may be used without having any specific limitations.

According to the above-described configuration, the X-rays having a plurality of energy levels which transmits the object are detected to generate the first transmission image group including a plurality of transmission image for the object.

Further, the first transmission image group is generated by detecting X-rays irradiated onto the object in various directions so that the first transmission image group may be configured to include a plurality of transmission images.

Next, in step S1300, when the first transmission image group is used, a tomographic image with an improved contrast of the soft tissue of the object may be reconstructed as compared with an example which uses a transmission image by one X-ray among X-rays having a plurality of energy levels.

Figure 3:
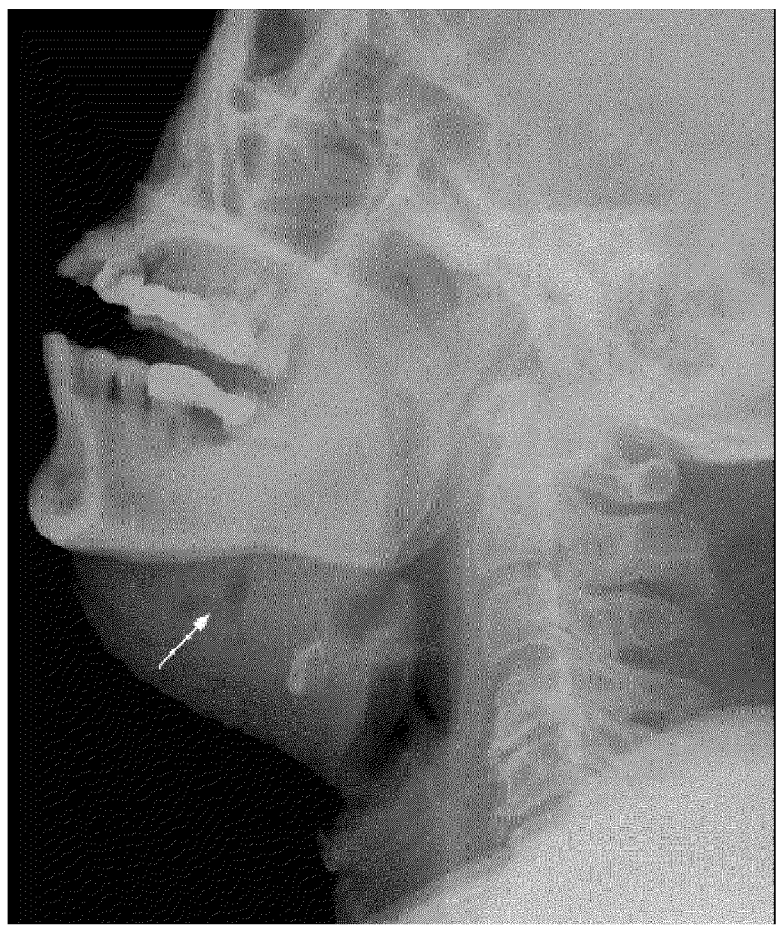
FIG. 3 is a view provided to explain a contrast characteristic of the soft tissue in an X-ray transmission image according to the related art.

As illustrated in FIG. 3, at an X-ray energy level (80 to 140 kVp) which is generally used during the computed tomography (CT), differently from hard tissue such as a bone, X-ray attenuation is significantly low in soft tissue such as skin or fat and thus a contrast of the soft tissue is significantly lowered as compared with the hard tissue. Therefore, it is difficult to detect an accurate interface of the soft tissue such as the skin of an object. Further, in order to automatically detect an interface using a computer algorithm, it is advantageous when the interface of the soft tissues represented in an image is distinct.

Figure 4:
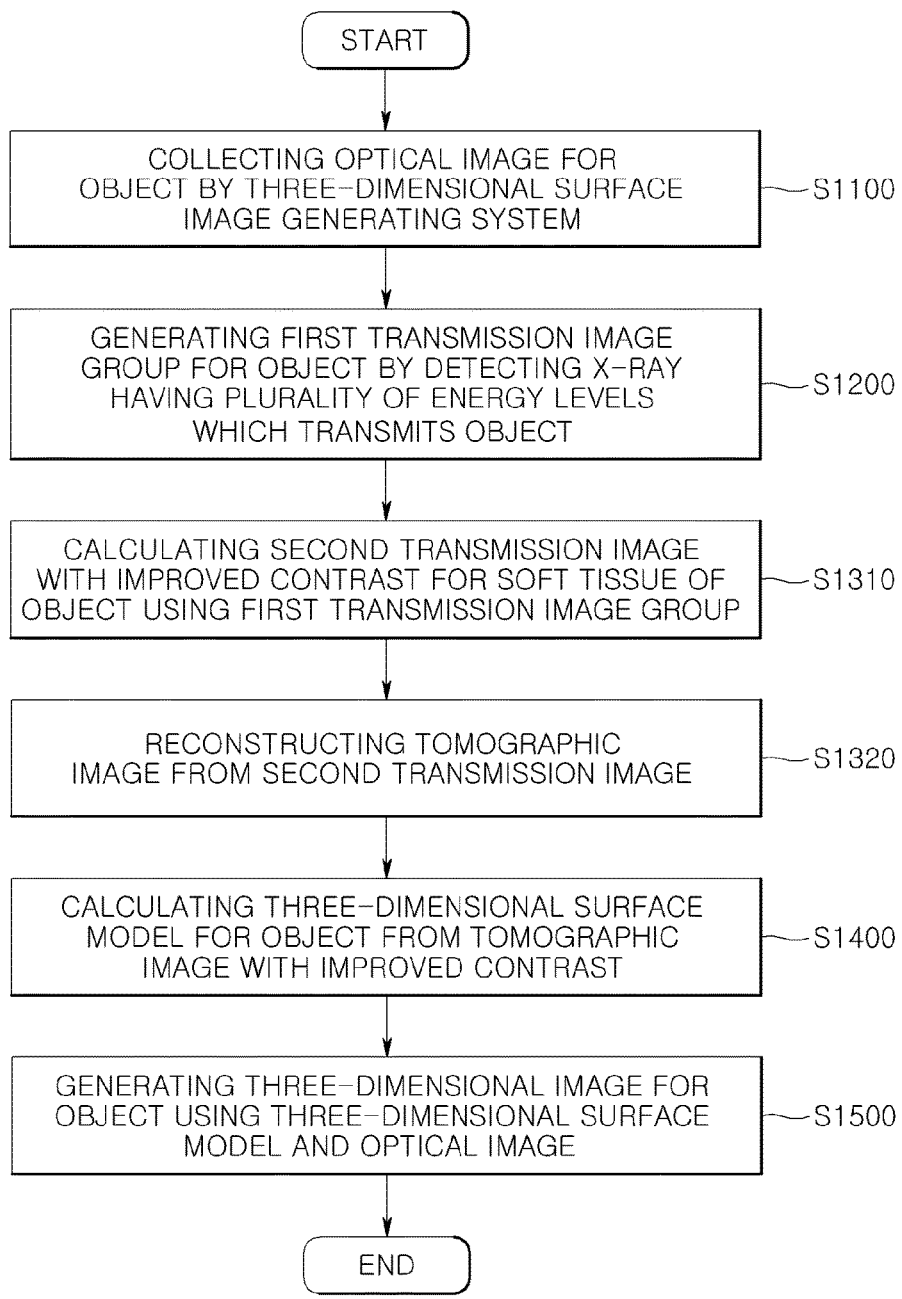
FIG. 4 is a flowchart of a detailed three-dimensional image generating method according to an exemplary embodiment of the present invention.

More specifically, FIG. 4 illustrates a flowchart of a three-dimensional image generating method in which the step S1300 is more specifically illustrated as an exemplary embodiment of the present invention.

As illustrated in FIG. 4, the step S1300 of reconstructing the three-dimensional image with the improved contrast includes a step S1310 of calculating a second transmission image an improved contrast for soft tissue such as the skin of the object using the first transmission image group, and a step S1320 of reconstructing a tomographic image from the second transmission image.

Therefore, in the step S1310, the second transmission image at a lower energy level in which a contrast for the soft tissue of the object is improved is calculated using the first transmission image group generated by detecting an X-ray having a plurality of energy levels, so that a monochromic X-ray transmission image with the improved contrast for the soft tissue of the object may be obtained.

To this end, in step S1310 of calculating the second transmission image, after generating a photoelectric absorption basis first image and a Compton scattering basis second image which is distinct at a higher energy level than that of the photoelectric absorption basis, the first image and the second image are linearly combined to calculate a virtual transmission image at a third energy level in which the contrast for the soft tissue of the object is improved.

In this case, the third energy level may be a low virtual energy level (for example, 20 keV to 40 keV) which is hard to be actually obtained in the three-dimensional image generating system. Alternatively, an energy level which may be lower than a lowest energy level available in the three-dimensional image generating system to improve the contrast for the soft tissue of the object may be selected.

In the meantime, the virtual transmission image at the third energy level may be adjusted to be at an arbitrary energy level by linearly combining the first image and the second image in order to minimize image artifacts such as beam hardening or metal artifact which may be generated when the X-ray tomographic image is reconstructed, in consideration of the characteristic of the object. Further, as the third energy level, an energy level which is higher than a lowest energy level available in the three-dimensional image generating system is used, so that the influence of the image artifacts may be minimized.

Further, instead of generating a virtual monochromic X-ray transmission image, a material decomposition technique which selectively separates a specific tissue or material such as a surface of the skin or a contrast media may be applied.

Figure 6A:
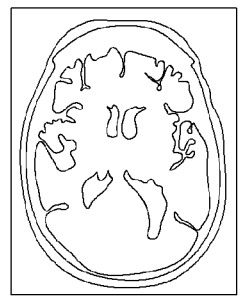
FIGS. 6A, 6B and 6C are a view of provided to explain a three-dimensional image generating method according to an exemplary embodiment of the present invention.

Next, in step S1320, a tomographic image is reconstructed from the second transmission image. As a method of reconstructing a tomographic image from the X-ray transmission image, various techniques of the related art are suggested and utilized. For example, methods which are capable of reconstructing a tomographic image from the X-ray transmission image, such as a filtered back projection technique including Feldkamp-Davis-Kress (FDK) reconstruction technique which has been generally frequently used, may be applied to this step without having any specific limitation. FIG. 6A illustrates a tomographic image of a head of an object which is generated using an X-ray transmission image.

Therefore, attenuation according to the energy level of the X-ray varies depending on a characteristic of a material such as soft tissue or hard tissue of the object. Therefore, in the present invention, after calculating a second transmission image with an improved contrast of the soft tissue of the object using the first transmission image group by virtually generating an X-ray transmission image at low energy (for example, 40 to 60 kVp) at which the contrast for the soft tissue may be increased and reconstructing the tomographic image using the second transmission image, the three-dimensional surface model for the object is generated. Therefore, an error incurred when the three-dimensional surface model for the object is generated using a computed tomographic image of the related art may be considerably improved.

That is, the plurality of energy levels in the first transmission image group includes the first energy level and the second energy level which is lower than the first energy level. Therefore, in the step of generating a second transmission image, a virtual (that is, a third energy level X-ray is not detected and generated) transmission image at the third energy level which is lower than the second energy level may be calculated.

Figure 5:
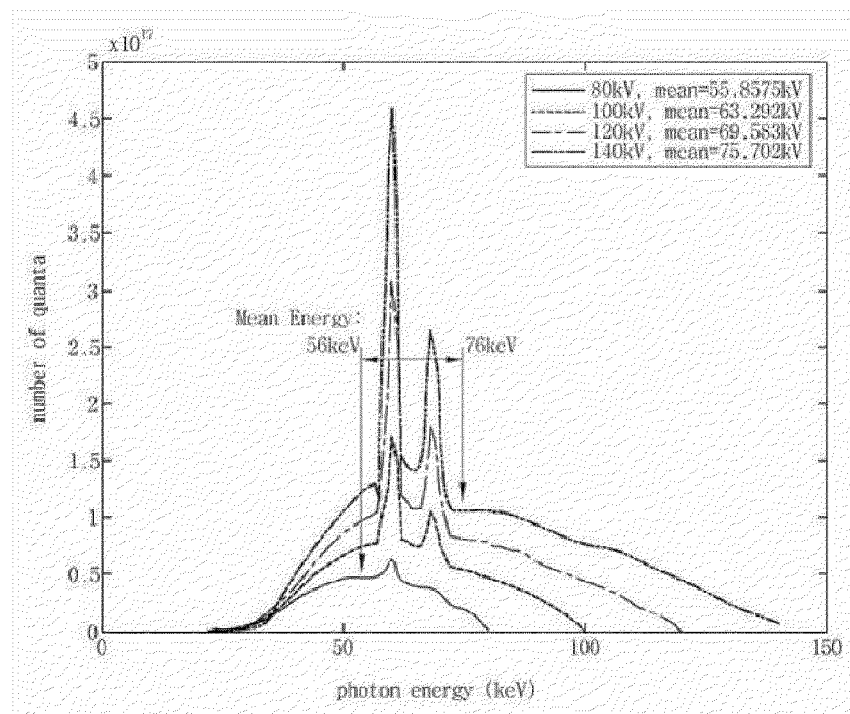
FIG. 5 is a view of an X-ray energy distribution example in a general X-ray tomographic imaging system.

More specifically, as illustrated in FIG. 5, in a general X-ray tomography system, an X-ray at an energy level of 80 to 140 kVp (here, kVp refers to a maximum value of an X-ray photon energy emitted from an X-ray source as a maximum tube voltage) is used. Therefore, as seen from FIG. 3, the contrast may be lowered because the X-ray attenuation in the soft tissue is low. However, in the present invention, after generating the first transmission image group generated by detecting an X-ray having a plurality of energy levels in a band of 80 to 140 kVp, a tomographic image with an improved contrast for the soft tissue of the object is reconstructed using the first transmission image group. Therefore, the error which may be incurred when the three-dimensional surface model for the object is generated may be considerably improved.

Next, in step S1400, the three-dimensional surface model for the object may be calculated from the tomographic image.

In this case, a surface detecting algorithm is applied to the tomographic image to calculate the three-dimensional surface model for the object. More specifically, one point or a partial region of an empty space (air) obtained by excluding a region of the object from the tomographic image is considered as a seed and the soft tissue is set as a limit of the area to perform a 3D region growing method and detect an interface between the empty space and the soft tissue. Therefore, the three-dimensional surface model for the object may be efficiently calculated.

Further, as the surface detecting algorithm, various segmentation techniques may be applied in addition to the above-described three-dimensional region growing method.

For example, in order to increase resolution of the interface, a deconvolution processing technique may be applied by predicting a point spread function is predicted or a Hessian filter which emphasizes a specific geometric surface structure to process may be applied.

Figure 6B:
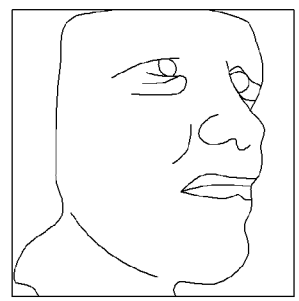

FIG. 6B illustrates a three-dimensional surface model for the object calculated from the tomographic image (see FIG. 6A) for the head of the object. The three-dimensional surface model may include three-dimensional shape data which configures the surface of the object as a three-dimensional shape.

Further, as an exemplary embodiment of the present invention, in consideration of information on a surface interface by the first transmission image group and surface contour information calculated from the optical image, the three-dimensional surface model for the object is corrected, thereby improving accuracy of the three-dimensional surface model.

More specifically, FIG. 8 illustrates a flowchart of a method of correcting a three-dimensional surface model for an object using an optical image according to an exemplary embodiment of the present invention. As seen from FIG. 8, after calculating an error from the surface interface information by the tomographic image and the surface contour information calculated from the optical image, the error is reflected to update the tomographic image. The above processes are repeated until the updated tomographic image satisfies a predetermined convergence condition to increase accuracy of the three-dimensional surface model for the object. Further, as a similar method, the surface interface information by the first transmission image is used to increase accuracy of the three-dimensional surface model for the object.

More specifically, FIG. 7 illustrates a flowchart of another three-dimensional image generating method in which the step S1300 is more specifically illustrated as another exemplary embodiment of the present invention.

As seen from FIG. 7, the step S1300 of reconstructing the tomographic image with the improved contrast may include a step S1330 of reconstructing a tomographic image group for a transmission image at a plurality of energy levels in the first transmission group and a step S1340 of reconstructing a tomographic image with the improved contrast for the soft tissue of the object using the tomographic image group for the transmission image at the plurality of energy levels.

Therefore, in step S1330, a tomographic image group including a plurality of tomographic images for each energy level is reconstructed using transmission images at the plurality of energy levels in the first transmission image group. Next, in step S1340, a tomographic image with an improved contrast for the soft tissue such as the skin of the object is reconstructed using the tomographic image group with the plurality of energy levels. Therefore, a three-dimensional surface model with improved accuracy for the surface of the object may be calculated.

However, it is not necessary to generate the three-dimensional surface model for the object the reconstructed tomographic image after reconstructing the tomographic image using the X-ray transmission image group for the object with a plurality of energy levels in the present invention. That is, in the present invention, it is possible to generate the three-dimensional surface model for the object using data included in the X-ray transmission image group after generating the X-ray transmission image group for the object at the plurality of energy levels, without performing the step of reconstructing the tomographic image for the object. In this case, the three-dimensional surface model is generated by processing only necessary data for generating the three-dimensional surface model without performing the process of reconstructing the entire tomographic image for the object so that the three-dimensional surface model may be quickly generated using only a small amount of computer resources.

Figure 6C:
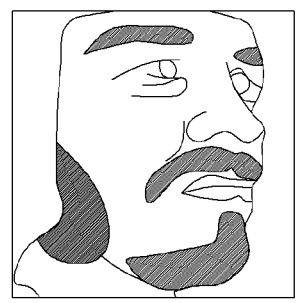

Finally, in step S1500, a three-dimensional image for the object may be generated using the three-dimensional surface model and the optical image. For example, the three-dimensional image may be generated by mapping a color image included in the optical image to the three-dimensional surface model for the object which is generated through a series of steps. FIG. 6C illustrates a three-dimensional image of a head of the object generated using the three-dimensional surface model and the optical image.

However, the present invention is not necessarily limited to generating the three-dimensional image in which the three-dimensional surface model and the optical image are combined but the three-dimensional image and the tomographic image for the object are separately provided to the user or one image generated by combining the three-dimensional image and the tomographic image may be further provided to the user.

Further, according to the present invention, the color information of the optical image may be combined to be represented in the three-dimensional surface model and the color information of the optical image and anatomical tomographic image information may be represented together in the three-dimensional surface model. Further, a material selective image which is separated during the multi-energy X-ray reconstructing step may be included. Here, the material selective image may refer to a nerve or a blood vessel structure which is emphasized using contrast enhancement.

Moreover, as an exemplary embodiment of the present invention, several configurations which further increase an accuracy of the three-dimensional surface model may be further included.

Figure 9:
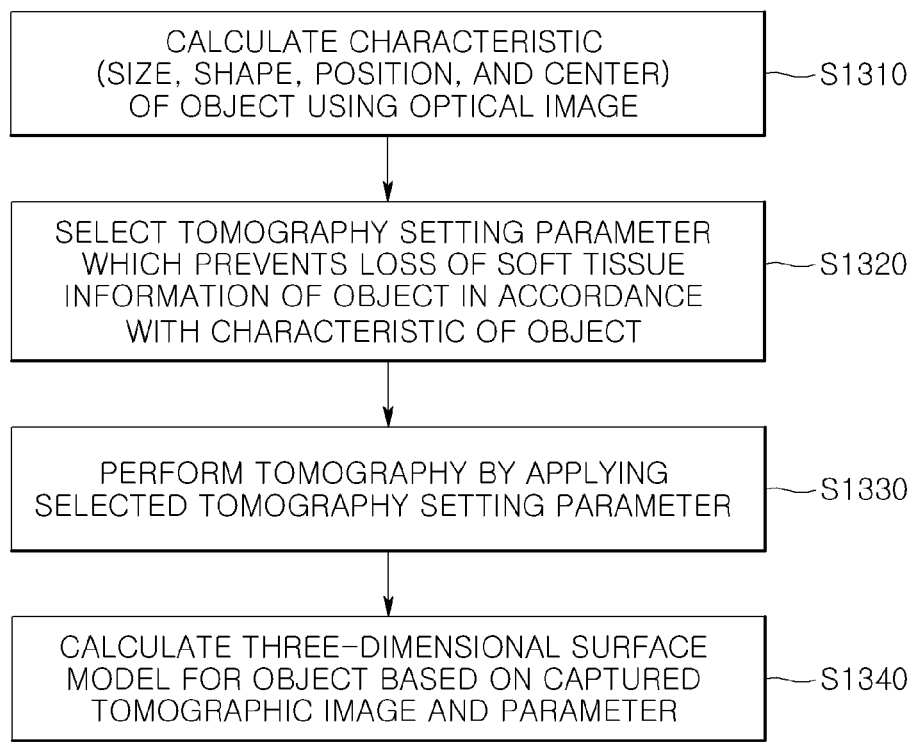
FIG. 9 is a flowchart of a method of applying an X-ray imaging setting parameter which is optimized by reflecting a characteristic of an object according to an exemplary embodiment of the present invention.

More specifically, FIG. 9 illustrates a flowchart of a method of applying an X-ray imaging setting parameter, such as an optimized X-ray exposing setting, by reflecting a characteristic of an object. As seen from FIG. 9, characteristics of an object, such as a size, a shape, a position, and a center of the object are calculated from the optical image collected using optical equipment such as a camera and an optimized X-ray imaging setting parameter is selected and applied to increase a contrast of the soft tissue of the object in consideration of the calculated characteristics of the object and then the X-ray imaging is performed to generate a three-dimensional surface model, thereby calculating a three-dimensional surface model having higher accuracy. For example, the X-ray exposing setting value may include a tube voltage (kVp) of the X-ray tube, a tube current (mA), or an exposure time. Furthermore, the optimized X-ray imaging setting parameter is calculated in advance to be stored as a table or implemented as a function to be used.

For example, when a charge integration detector is used, a filter setting parameter such as a tube voltage kVp in accordance with the characteristic of the object may be applied. When the photon counting detector is used, the tube voltage kVp in accordance with the characteristic of the object and a filter and energy identification threshold setting parameter are applied together so that the accuracy of the three-dimensional surface model may be further improved.

Further, in the step of generating the first transmission image group, the surface contour information of the object calculated from the optical image and preshot X-ray image information for the object are compared to adjust the X-ray exposure so that the X-ray detector operates on the surface of the object in a dynamic range where the soft tissue information is included in the first transmission image group as much as possible. Therefore, loss of information on the soft tissue such as the skin of the object may be minimized in the first transmission image group.

In the present invention, various optical equipment may be used to collect the optical image. For example, a CCD or CMOS sensor which may collect visible rays may be used. An optical image sensor in an infrared ray region (for example, near infrared ray) which may obtain subcutaneous tissue information of the object may be used. A spectroscopy detector or an array thereof which may collect various wavelength information by one sensor may be used. Further, an infrared sensor is used to collect image information such as blood vessel distribution below the skin.

Figure 10:
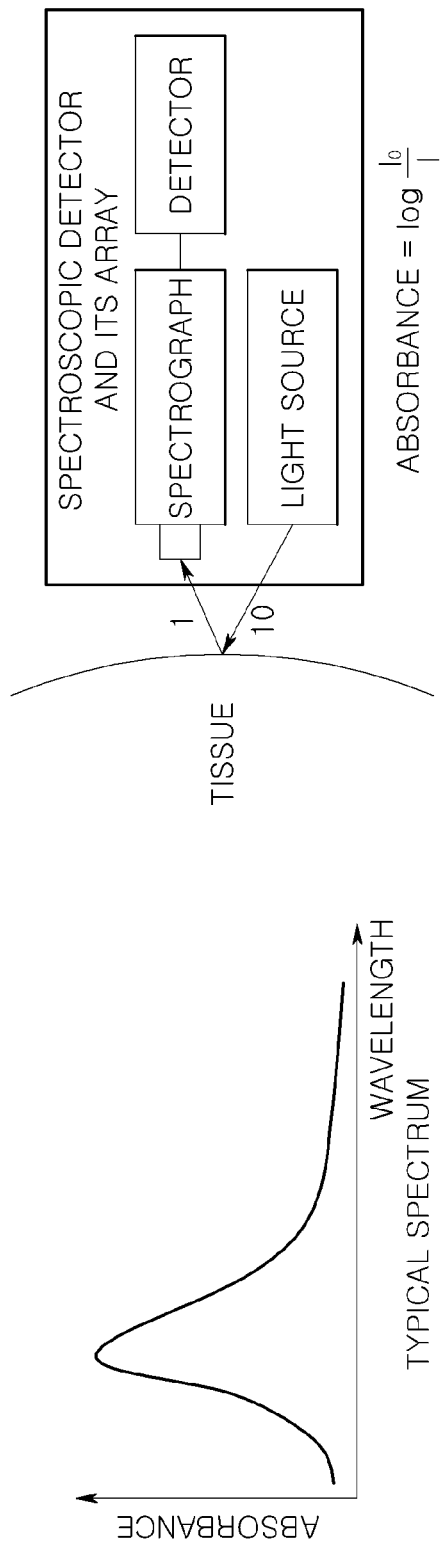
FIGS. 10A and 10B are a view provided to explain a method of collecting an optical image using a spectroscopy detector according to an exemplary embodiment of the present invention.

FIG. 10A and FIG. 10B explain a method of collecting an optical image using a spectroscopy detector according to an exemplary embodiment of the present invention. As seen from FIG. 10A and FIG. 10B, when the optical image is collected using the spectroscope detector, spectrum information in various wavelengths may be collected. Therefore, a photo reaction characteristic of the surface of the object is characterized so that data having various purposes may be calculated.

Moreover, as an exemplary embodiment of the present invention, as the optical image, an image obtained using a visible ray or an infrared ray is used or the spectroscopic image is used so that various information may be provided according to the purpose of the image.

Moreover, in the three-dimensional image, a contrast for a specific soft tissue is improved using a multi-energy X-ray having a plurality of energy levels, to provide lesion information on a nerve, a blood vessel, or a contrast enhanced lesion or provide anatomical information on a specific tissue.

Figure 11:
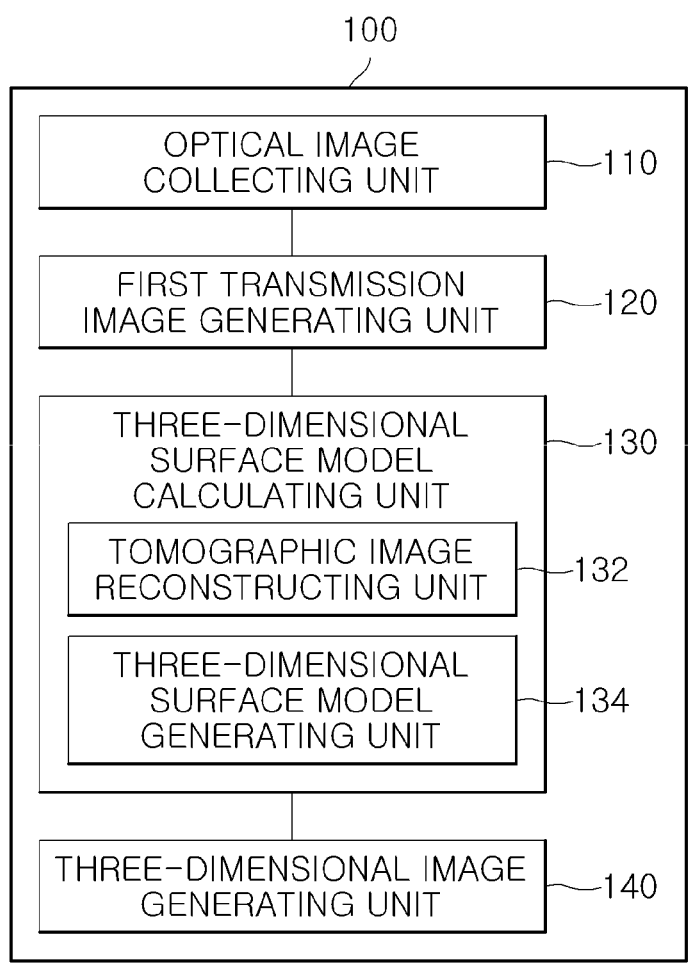
FIG. 11 is a view of a configuration of a three-dimensional image generating system according to an exemplary embodiment of the present invention.

FIG. 11 illustrates a view of a configuration of a three-dimensional image generating system 100 according to an exemplary embodiment of the present invention. As seen from FIG. 9, the three-dimensional image generating system includes an optical image collecting unit 110, a first transmission image generating unit 120, a three-dimensional surface model calculating unit 130, and a three-dimensional image generating unit 140.

First, the optical image collecting unit 110 collects an optical image including surface color information for the object.

Next, the first transmission image generating unit 120 detects an X-ray having a plurality of energy levels which transmits the object to generate a first transmission image group for the object.

Further, the three-dimensional surface model calculating unit 130 calculates a three-dimensional surface model for the object using the first transmission image group. In this case, the three-dimensional surface model calculating unit 130 may include a tomographic image reconstructing unit 132 which reconstructs a tomographic image with an improved contrast for the soft tissue of the object using the first transmission image group and a three-dimensional surface model generating unit 134 which generates a three-dimensional surface model for the object from the tomographic image with an improved contrast.

Further, the tomographic image reconstructing unit 132 includes a second transmission image calculating unit (not illustrated) which uses the first transmission image group to calculate a second transmission image with an improved contrast for the soft tissue of the object as compared with an example in which one transmission image in the first transmission image group is used and a tomographic image calculating unit (not illustrated) which reconstructs and calculates a tomographic image for the object from the second transmission image. The tomographic image reconstructing unit 132 includes a tomographic image group reconstructing unit (not illustrated) which reconstructs a tomographic image group for a transmission image at a plurality of energy levels in the first transmission image group and a tomographic image generating unit (not illustrated) which generates a tomographic image with an improved contrast for the soft tissue of the object using the tomographic image group for the transmission image at the plurality of energy levels.

Finally, the three-dimensional image generating unit 140 generates a three-dimensional image for the object using the three-dimensional surface model and the optical image.

The three-dimensional image generating system 100 according to the exemplary embodiment of the present invention expands or is implemented similarly to the three-dimensional image generating method according to the exemplary embodiment of the present invention which has been described in detail above so that detailed description thereof will be omitted.

Figure 12:
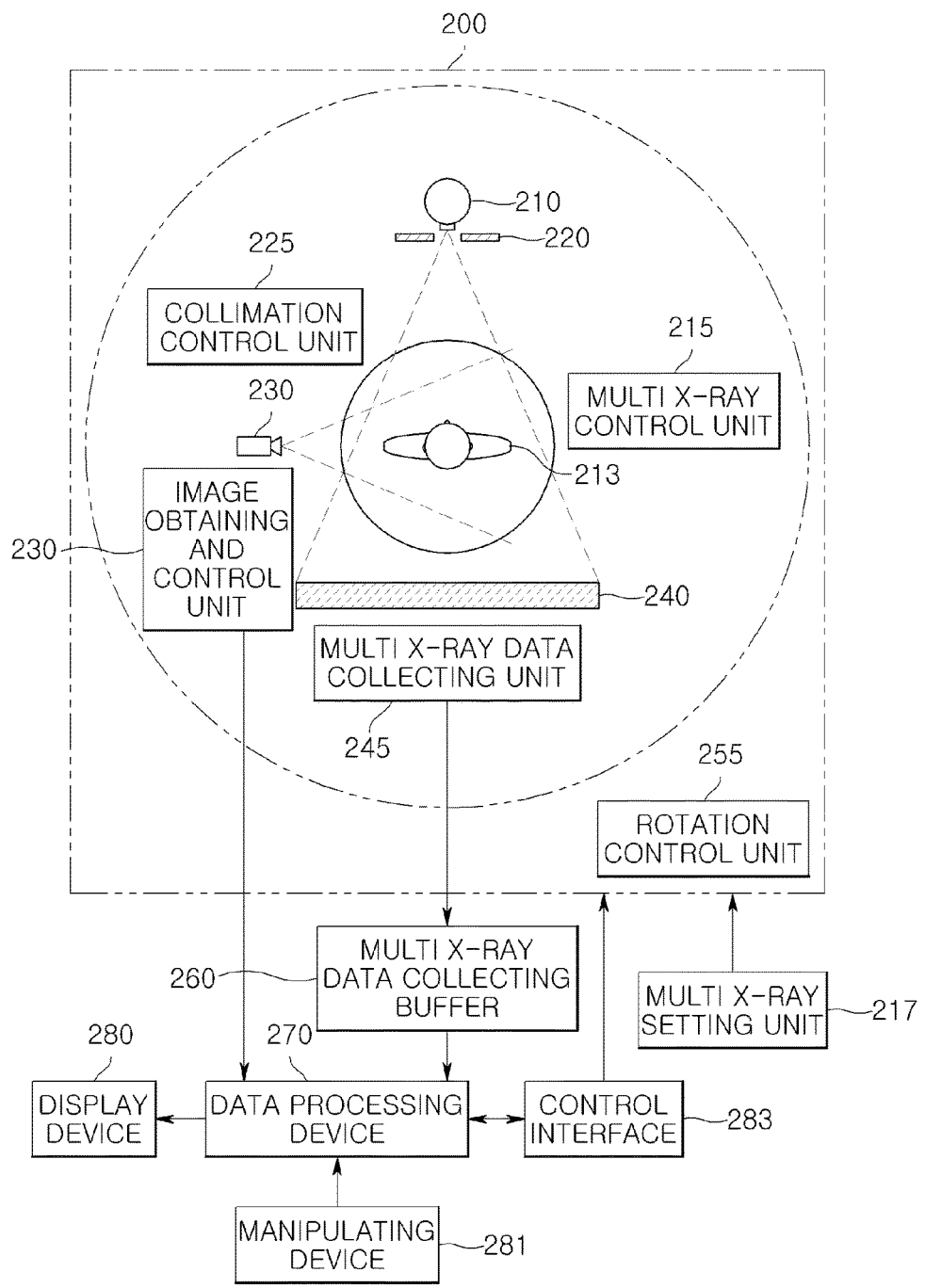
FIG. 12 is a view of a configuration of a multi-energy X-ray imaging device which generates a three-dimensional image according to an exemplary embodiment of the present invention.

FIG. 12 illustrates a view of a configuration of a multi-energy X-ray imaging device 200 which generates a three-dimensional image according to an exemplary embodiment of the present invention.

Hereinafter, components of the multi-energy X-ray imaging device 200 according to an exemplary embodiment of the present invention will be described in more detail with reference to FIGS. 11 and 12.

As seen from FIG. 12, the multi-energy X-ray imaging device 200 which generates a three-dimensional image according to an exemplary embodiment of the present invention includes a multi X-ray source 210 which emits an X-ray having a plurality of energy levels in accordance with control of a multi-X-ray control unit 215, a collimator 220 which adjusts collimation in accordance with control of a collimation control unit 225, a multi X-ray detector 240 which detects an X-ray having a plurality of energy levels which transmits an object 213, a multi X-ray data collecting unit 245 which collects transmission data of the detected X-ray having a plurality of energy levels, an image camera 230 which collects an optical image including surface color information on the object 213, an image obtaining and control unit 235 which processes the collected optical image, and a rotator 250 which is mounted with components to rotate around the object in accordance with control of a rotation control unit 255.

Further, the multi-energy X-ray imaging device 200 may further include a multi X-ray data collecting buffer 260 which temporally stores the transmission data of the X-ray having a plurality of energy levels collected in the multi X-ray data collecting unit 245, a data processing device 270 which processes the transmission data information of the X-ray having the plurality of energy levels transmitted from the multi X-ray data collecting buffer 260 and the image obtaining and control unit 235 and optical image information to reconstruct as a three-dimensional image for the object, a display device 280 which displays the three-dimensional image for the object, a control interface 283 which serves as an interface when the data processing device 270 controls the rotator 250 and the components (multi X-ray source 210, the collimator 220, and the image camera 230) mounted on the rotator 250, a manipulating device 281 which includes manipulation buttons of a user, and a multi X-ray setting unit 217. The multi X-ray control unit 215, the multi X-ray source 210, the collimation control unit 225, the collimator 220, the image camera 230, the image obtaining and control unit 235, the multi X-ray detector 240, and the multi X-ray data collecting unit 245 are mounted on the rotator 250 to rotatably operate in accordance with the control of the rotation control unit 255.

That is, the rotator 250 in which the above-mentioned components are mounted simultaneously and consistently obtains X-ray transmission data and optical image information including the surface color information for the object 213 in each position while rotating around the object 213 at a minute angle interval.

The multi X-ray source 210 generates a predetermined X-ray in accordance with the control of the X-ray control unit 215 to emit the X-ray toward the object 213. In this case, attenuation of the X-ray varies according to the energy levels of the X-ray which transmits the tissue in accordance with the characteristic of the tissue which configures the object 213. Specifically, differently from a hard tissue such as a bone, an X-ray attenuation in the soft tissue such as the skin is considerably low and thus a contrast of the soft tissue is significantly lowered. Therefore, it is difficult to accurately detect an accurate interface of the soft tissue such as the skin of an object.

Therefore, the multi X-ray source 210 and the multi X-ray detector 240 according to the present invention irradiate the X-ray having at least two energy levels onto the object by reflecting the above-mentioned characteristic and detect X-ray transmission data in a band including two or more energy levels for the X-ray which transmits the object to generate a first transmission image for the object.

More specifically, in the multi X-ray source 210, an operation mode is switched to release the X-ray having different energy levels (for example, 8 kVp and 12 kVp) or a filter is added to the multi X-ray source 210 to release the X-ray having a plurality of different energy levels. Moreover, the three-dimensional image generating system 200 may include a plurality of X-ray sources 210 having different energy levels.

Further, the multi X-ray detector 240 may be configured using a photon counting detector which may discern and measure the energy level for an incident photon or a multi X-ray detector 240 in which detectors which detect a plurality of energy levels form a laminated structure is configured to detect an X-ray having a plurality of energy levels. Furthermore, the photo counting detector and a charge integration detector are combined to configure a detector.

Further, radiation which is irradiated from the multi X-ray source 210 to the object 213 may include multi-energy X-ray or polychromatic X-ray. The X-ray transmits the object 213 through the collimator 220 which adjusts collimation in accordance with the control of the collimation control unit 225 to be transmitted to the multi X-ray detector 240. The collimator 220 is appropriately collimated in consideration of a shape of a region of interest (ROI) in the object to transmit the X-ray.

The X-ray transmission data which transmits the object detected by the multi X-ray detector 240 is collected by the multi X-ray data collecting unit 245.

The multi X-ray data collecting unit 245 converts a series of voltage signals generated in accordance with an amount of X-ray detected in the multi X-ray detector 240 into a predetermined digital signal to transmit the digital signal to the multi X-ray data collecting buffer 260. The multi X-ray data collecting buffer 260 sequentially transmits the digital signal on the X-ray transmission data information for the object to the data processing device 270.

In the meantime, the image camera 230 mounted on the rotator 250 images and obtains optical information including surface color information of the object 213 to transmit the optical information to the image obtaining and control unit 235. The image obtaining and control unit 235 temporally stores the optical information including the surface color information obtained by the image camera 230 and sequentially transmits the optical information to the data processing device 270.

A focal point and an angle of the image camera 230 are adjusted in accordance with control of the image obtaining and control unit 235 to accurately photograph the optical image including the surface color information of the object 213. That is, when the size and the position of the object 213 are changed, the focal point and the angle of the image camera 230 are adjusted again in accordance with the control of the image obtaining and control unit 235 to accurately photograph the optical image including the surface color information of the object 213.

An image sensor used in the image camera 230 may be one of a charge coupled device (CCD) and a complementary metal oxide semiconductor field effect transistor (CMOS). In addition to this, various sensors which accurately collect the optical image including the surface color information for the object may be used.

The image camera 230 may be provided in a predetermined position of the rotator 250 and may be provided so as not to be hit by the X-ray which is irradiated from the multi X-ray source 210. Further, a lens of the image camera 230 may be provided to be consistent with a rotational center of the rotator 250, in order to accurately photograph the optical image including the surface color information of the object 213.

The data processing device 270 generates a three-dimensional image for the object using the X-ray transmission data for the object 213 and the optical image information for the objet 213 which are transmitted.

More specifically, as an exemplary embodiment of the present invention, the data processing device 270 reconstructs a tomographic image with an improved contrast for the soft tissue of the object 213 using the X-ray transmission data having a plurality of energy levels which transmits the object 213 and then calculates a three-dimensional surface model for the object 213 by applying a surface detection algorithm to the tomographic image. Furthermore, the data processing device 270 generates a three-dimensional image for the object 213 using the three-dimensional surface model and the optical image including the surface color information for the object 213.

Therefore, actual color information may be mapped to a three-dimensional image generated by the data processing device 270 and further plentiful surface information such as the eyebrow, hair, or make-up, a sentence, or paintings of a human which is hard to be reproduced in the X-ray tomographic image may be reproduced with actual color.

Further, the data processing device 270 not only generates the three-dimensional image by combining the three-dimensional surface model and the optical image, but also simultaneously generates a tomographic image for the object together with the three-dimensional image. Furthermore, the data processing device 270 generates an image obtained by combining the three-dimensional image and the tomographic image and provides the image to the user. It will be appreciated that various exemplary embodiments of the present invention have been described herein for purposes of illustration, and that various modifications, changes, and substitutions may be made by those skilled in the art without departing from the scope and spirit of the present invention. Accordingly, the exemplary embodiments described in the present invention should not be construed as limiting the technical spirit of the present invention but explaining the technical spirit, and is not limited by the exemplary embodiments. The scope of the present invention may be interpreted by the appended claims and the technical spirit in the equivalent range is intended to be embraced by the invention.

The invention claimed is:

1. A three-dimensional image generating method comprising:
   collecting optical image of an object, by a three-dimensional image generating system;
   detecting X-ray having a plurality of energy levels which transmits the object to generate a first transmission image group for the object;
   calculating a three-dimensional surface model for the object using the first transmission image group; and
   generating a three-dimensional image for the object using the three-dimensional surface model and the optical image,
   wherein calculating the three-dimensional surface model includes reconstructing a tomographic image with improved contrast of soft tissue of the object using the first transmission image group, as compared with an example which uses a transmission image by one X-ray among X-rays having a plurality of energy levels, and
   wherein reconstructing the tomographic image with an improved contrast includes:
   calculating a second transmission image with an improved contrast for a surface tissue of the object using the first transmission image group; and
   reconstructing a tomographic image from the second transmission image.

2. The method of claim 1, wherein the calculating of a three-dimensional surface model further includes:
   calculating a three-dimensional surface model for the object from the tomographic image with an improved contrast.

3. The method of claim 2, wherein the reconstructing of a tomographic image with an improved contrast includes:
   reconstructing a tomographic image group for a transmission image with a plurality of energy levels in the first transmission image group; and
   reconstructing a tomographic image with an improved contrast for the soft tissue of the object using a tomographic image group for a transmission image of a plurality of energy levels.

4. The method of claim 2, wherein the plurality of energy levels includes a first energy level and a second energy level which is lower than the first energy level, and
   in the calculating of the second transmission image, a virtual second transmission image at a third energy level which is lower than the second energy level is calculated.

5. The method of claim 2, wherein in the calculating of the second transmission image, a first image corresponding to a photoelectric absorption basis and a second image corresponding to a Compton scattering basis are generated and the first image and the second image are linearly combined to calculate a virtual second transmission image at a third energy level.

6. The method of claim 5, wherein the third energy level is lower than a lowest energy level which is available in the three-dimensional image generating system.

7. The method of claim 1, wherein in the generating of the first transmission image group, a photon counting X-ray detector or an X-ray detector having a laminated structure which detects a plurality of energy levels is used to simultaneously detect X-rays having a plurality of energy levels.

8. The method of claim 1, wherein in the generating of the first transmission image group, an X-ray is irradiated by switching an operation mode of the X-ray source to emit the X-ray having different energy levels, switching a filter by adding a multiple filter to the X-ray source to emit the X-ray having a plurality of different energy levels, or using a plurality of X-ray sources having different energy levels.

9. The method of claim 1, wherein in the calculating of a three-dimensional surface model, a surface detecting algorithm is applied to the tomographic image to calculate the three-dimensional surface model.

10. The method of claim 9, wherein one point or a partial region of an empty space (air) obtained by excluding a region of the object from the tomographic image is considered as a seed and a surface of the soft tissue is set as a limit of the region to perform a 3D region growing method and detect an interface between the empty space and the soft tissue, thereby calculating the three-dimensional surface model.

11. The method of claim 1, wherein in the calculating of a three-dimensional surface model, a three-dimensional surface model for the object is corrected based on surface interface information by the first transmission image and surface contour information calculated from the optical image.

12. The method of claim 11, wherein the calculating of a three-dimensional surface model includes:
a first step of calculating an error of the surface interface information by the tomographic image and the surface contour information calculated from the optical image;
a second step of updating the tomographic image by reflecting the error; and
a step of repeating the first step and the second step until the updated tomographic image satisfies a predetermined convergence condition.

13. The method of claim 1, wherein in the generating of the first transmission image, the surface contour information of the object calculated from the optical image and preshot X-ray image information for the object are compared to adjust X-ray exposure so that the X-ray detector operates on the surface of the object in a dynamic range where the soft tissue information is included in the first transmission image group as much as possible.

14. The method of claim 1, wherein an X-ray exposure setting value required to calculate the three-dimensional surface model for the object in accordance with a characteristic of the object is stored in advance and the X-ray exposure setting value is applied in consideration of the characteristic of the object figured out using the optical image on the object.

15. The method of claim 1, wherein the optical image includes information on a structure of a surface lower part of the object using infrared ray.

16. The method of claim 1, wherein the optical image includes one or more of images using a visible ray or an infrared ray and a spectroscopic image.

17. The method of claim 1, wherein the three-dimensional image includes anatomical information or lesion information on a nerve, a blood vessel, or a specific soft tissue or contrast enhanced lesion information.

18. A three-dimensional image generating system which generates a three-dimensional image for an object, the system comprising:
an optical image collecting unit which collects optical image for an object;
a first transmission image generating unit which detects X-ray having a plurality of energy levels which transmits the object to generate a first transmission image group for the object;
a three-dimensional surface model calculating unit which calculates a three-dimensional surface model for the object using the first transmission image group; and
a three-dimensional image generating unit which generates a three-dimensional image for the object using the three-dimensional surface model and the optical image,
wherein the three-dimensional surface model calculating unit includes a tomographic image reconstructing unit which reconstructs a tomographic image with an improved contrast of the soft tissue of the object using the first transmission image group, as compared with an example which uses a transmission image by one X-ray among X-rays having a plurality of energy levels, and
wherein the tomographic image reconstructing unit includes:
a second transmission image calculating unit which calculates a second transmission image with an improved contrast for the soft tissue of the object using the first transmission image group; and
a tomographic image calculating unit which reconstructs and calculates a tomographic image for the object from the second transmission image.

19. The system of claim 18, wherein the three-dimensional surface model calculating unit further includes:
a three-dimensional surface model generating unit which generates a three-dimensional surface model for the object from the tomographic image with an improved contrast.

20. The system of claim 19, wherein the tomographic image reconstructing unit includes:
a tomographic image group reconstructing unit which reconstructs a tomographic image group for a transmission image of a plurality of energy levels in the first transmission image group; and
a tomographic image generating unit which generates a tomographic image with an improved contrast for the soft tissue of the object using a tomographic image group for a transmission image of a plurality of energy levels.

* * * * *